US010449065B2

(12) United States Patent
Knapp et al.

(10) Patent No.: US 10,449,065 B2
(45) Date of Patent: Oct. 22, 2019

(54) METHOD OF MANUFACTURING A TUBULAR MEDICAL IMPLANT

(71) Applicant: SMed-TA/TD, LLC, Columbia City, IN (US)

(72) Inventors: Troy D. Knapp, Alachua, FL (US); Gregory C. Stalcup, Fort Wayne, IN (US); Joseph Jurick, Fort Wayne, IN (US); Paul S. Nebosky, Fort Wayne, IN (US)

(73) Assignee: SMed-TA/TD, LLC, Columbia City, IN (US)

( * ) Notice: Subject to any disclaimer, the term of this patent is extended or adjusted under 35 U.S.C. 154(b) by 181 days.

(21) Appl. No.: 15/620,226

(22) Filed: Jun. 12, 2017

(65) Prior Publication Data
US 2017/0273808 A1    Sep. 28, 2017

Related U.S. Application Data

(62) Division of application No. 14/204,056, filed on Mar. 11, 2014, now Pat. No. 9,681,966.
(Continued)

(51) Int. Cl.
*A61F 2/852* (2013.01)
*A61F 2/82* (2013.01)
(Continued)

(52) U.S. Cl.
CPC ............ *A61F 2/852* (2013.01); *A61F 2/2846* (2013.01); *A61F 2/82* (2013.01);
(Continued)

(58) Field of Classification Search
CPC .. A61F 2/2846; A61F 2/82; A61F 2210/0076; A61F 2002/30235;
(Continued)

(56) References Cited

U.S. PATENT DOCUMENTS 3,855,638 A   12/1974  Pilliar
3,867,728 A    2/1975  Stubstad et al.
(Continued)

FOREIGN PATENT DOCUMENTS

EP   0 938 879 A2   9/1999
WO   03/026714 A1   4/2003

OTHER PUBLICATIONS

Bryan, R.S. et al. "The Effect of Polyvinyl-Formal (Ivalon) Sponge on Cortical Bone Healing." Proceedings of the Staff Meetings of the Mayo Clinic vol. 33 (1958): 453-457 (3 pages).
(Continued)

*Primary Examiner* — George J Ulsh
(74) *Attorney, Agent, or Firm* — Taylor IP, P.C.

(57) ABSTRACT

A method of manufacturing a tubular medical implant is provided. The method includes forming a hollow first tube with a first diameter and a first plurality of pores formed thereon and a hollow second tube with a second unstretched diameter and a second plurality of pores formed thereon. The second unstretched diameter is greater than the first diameter. At least a portion of the first tube slides within the second tube to create an overlapped area of the first tube and the second tube. The first tube and second tube are then bonded together in the overlapped area.

10 Claims, 7 Drawing Sheets

Related U.S. Application Data (60) Provisional application No. 61/788,738, filed on Mar. 15, 2013.

(51) Int. Cl.
*A61F 2/28* (2006.01)
*A61F 2/30* (2006.01)

(52) U.S. Cl.
CPC ............... *A61F 2002/3092* (2013.01); *A61F 2002/30235* (2013.01); *A61F 2002/30971* (2013.01); *A61F 2210/0076* (2013.01); *A61F 2250/0023* (2013.01)

(58) Field of Classification Search
CPC .... A61F 2002/3092; A61F 2002/30971; A61F 2250/0023; A61F 2/852; A61F 2/44; A61F 2/3094; A61F 2/00; A61F 2/01; A61F 2/02; A61F 2/04; A61F 2002/072; A61F 2/91; A61F 2240/00; A61L 27/56; B29C 43/00; B29C 2049/2047; B29C 31/002; B29C 33/485
USPC ........................................................ 623/1.15
See application file for complete search history.

(56) References Cited

U.S. PATENT DOCUMENTS

| | | | |
|---|---|---|---|
| 4,011,602 A | 3/1977 | Rybicki et al. | |
| 4,222,128 A | 9/1980 | Tomonaga et al. | |
| 4,608,052 A | 8/1986 | Van Kampen et al. | |
| 4,737,411 A | 4/1988 | Graves, Jr. et al. | |
| 4,769,041 A | 9/1988 | Morscher | |
| 4,846,834 A | 7/1989 | von Recum et al. | |
| 4,976,738 A | 12/1990 | Frey et al. | |
| 5,030,233 A | 7/1991 | Ducheyne | |
| 5,104,410 A | 4/1992 | Chowdhary | |
| 5,204,055 A | 4/1993 | Sachs et al. | |
| 5,219,363 A | 6/1993 | Crowninshield et al. | |
| 5,282,861 A | 2/1994 | Kaplan | |
| 5,380,328 A | 1/1995 | Morgan | |
| 5,490,962 A | 2/1996 | Cima et al. | |
| 5,496,372 A | 3/1996 | Hamamoto et al. | |
| 5,518,680 A | 5/1996 | Cima et al. | |
| 5,571,187 A | 11/1996 | Devanathan | |
| 5,637,175 A | 6/1997 | Feygin et al. | |
| 5,730,817 A | 3/1998 | Feygin et al. | |
| 5,732,469 A | 3/1998 | Hamamoto et al. | |
| 5,807,406 A | 9/1998 | Brauker et al. | |
| 5,824,054 A | 10/1998 | Khosravi et al. | |
| 5,869,170 A | 2/1999 | Cima et al. | |
| 5,876,550 A | 3/1999 | Feygin et al. | |
| 6,010,336 A | 1/2000 | Shimotoso et al. | |
| 6,136,029 A | 10/2000 | Johnson et al. | |
| 6,139,574 A | 10/2000 | Vacanti et al. | |
| 6,143,035 A | 11/2000 | McDowell | |
| 6,143,293 A | 11/2000 | Weiss et al. | |
| 6,176,874 B1 | 1/2001 | Vacanti et al. | |
| 6,261,320 B1 | 7/2001 | Tam et al. | |
| 6,306,424 B1 | 10/2001 | Vyakamam et al. | |
| 6,328,765 B1 | 12/2001 | Hardwick et al. | |
| 6,333,029 B1 | 12/2001 | Vyakamam et al. | |
| 6,337,198 B1 | 1/2002 | Levene et al. | |
| 6,365,149 B2 | 4/2002 | Vyakamam et al. | |
| 6,409,764 B1 | 6/2002 | White et al. | |
| 6,423,252 B1 | 7/2002 | Chun et al. | |
| 6,428,569 B1 | 8/2002 | Brown | |
| 6,440,734 B1 | 8/2002 | Pykett et al. | |
| 6,461,385 B1 | 10/2002 | Gayer et al. | |
| 6,471,993 B1 | 10/2002 | Shastri et al. | |
| 6,488,701 B1 | 12/2002 | Nolting et al. | |
| 6,514,514 B1 | 2/2003 | Atkinson et al. | |
| 6,520,997 B1 | 2/2003 | Pekkarinen et al. | |
| 6,526,984 B1 | 3/2003 | Nilsson et al. | |
| 6,527,810 B2 | 3/2003 | Johnson et al. | |
| 6,530,958 B1 | 3/2003 | Cima et al. | |
| 6,533,818 B1 | 3/2003 | Weber et al. | |
| 6,534,084 B1 | 3/2003 | Vyakamam et al. | |
| 6,544,472 B1 | 4/2003 | Compton et al. | |
| 6,554,857 B1 | 4/2003 | Zilla et al. | |
| 6,571,130 B1 | 5/2003 | Ljungstrom et al. | |
| 6,599,322 B1 | 7/2003 | Amrich et al. | |
| 6,626,950 B2 | 9/2003 | Brown et al. | |
| 6,673,108 B2 | 1/2004 | Zilla et al. | |
| 6,712,850 B2 | 3/2004 | Vyakamam et al. | |
| 6,783,546 B2 | 8/2004 | Zucherman et al. | |
| 6,852,272 B2 | 2/2005 | Artz et al. | |
| 6,881,413 B1 | 4/2005 | Bartholeyns | |
| 6,893,465 B2 | 5/2005 | Huang | |
| 6,993,406 B1 | 1/2006 | Cesarano, III et al. | |
| 7,018,418 B2 | 3/2006 | Amrich et al. | |
| 7,052,710 B2 | 5/2006 | Giordano et al. | |
| 7,087,200 B2 | 8/2006 | Taboas et al. | |
| 7,108,828 B2 | 9/2006 | Lefebvre et al. | |
| 7,174,282 B2 | 2/2007 | Hollister et al. | |
| 7,189,409 B2 | 3/2007 | Pirhonen et al. | |
| 7,208,222 B2 | 4/2007 | Rolfe et al. | |
| 7,250,060 B2 | 7/2007 | Trieu | |
| 7,384,786 B2 | 6/2008 | Freyman et al. | |
| 7,537,617 B2 | 5/2009 | Bindsell et al. | |
| 7,537,664 B2 | 5/2009 | O'Neill et al. | |
| 7,632,228 B2 | 12/2009 | Brauker et al. | |
| 7,666,230 B2 | 2/2010 | Orban et al. | |
| 7,674,426 B2 | 3/2010 | Grohowski, Jr. | |
| 7,674,477 B1 | 3/2010 | Schmid et al. | |
| 8,071,007 B1 | 12/2011 | Teoh et al. | |
| 2002/0072798 A1 | 6/2002 | Riesle et al. | |
| 2003/0130718 A1 | 7/2003 | Palmas et al. | |
| 2003/0171820 A1 | 9/2003 | Wilshaw et al. | |
| 2004/0044398 A1 | 3/2004 | Nicholas | |
| 2004/0191292 A1 | 9/2004 | Chou | |
| 2005/0085893 A1 | 4/2005 | Roy | |
| 2005/0100578 A1 | 5/2005 | Schmid et al. | |
| 2005/0177247 A1 | 8/2005 | Canham et al. | |
| 2005/0228503 A1 | 10/2005 | Gundolf | |
| 2005/0246032 A1 | 11/2005 | Bokros et al. | |
| 2006/0178744 A1 | 8/2006 | de Villiers et al. | |
| 2006/0282166 A1 | 12/2006 | Molz et al. | |
| 2007/0038299 A1 | 2/2007 | Stone et al. | |
| 2007/0105222 A1 | 5/2007 | Wolfinbarger et al. | |
| 2007/0173917 A1* | 7/2007 | Hayashi ............... A61F 2/07 623/1.1 |
| 2007/0179610 A1 | 8/2007 | Biedermann et al. | |
| 2007/0185585 A1 | 8/2007 | Bracy et al. | |
| 2007/0190880 A1 | 8/2007 | Dubrow et al. | |
| 2007/0191963 A1 | 8/2007 | Winterbottom et al. | |
| 2007/0196419 A1 | 8/2007 | Teller et al. | |
| 2007/0203584 A1 | 8/2007 | Bandyopadhyay et al. | |
| 2010/0042167 A1 | 2/2010 | Nebosky et al. | |
| 2010/0042215 A1 | 2/2010 | Stalcup et al. | |
| 2010/0042218 A1 | 2/2010 | Nebosky et al. | |
| 2010/0190254 A1 | 7/2010 | Chian et al. | |
| 2010/0291176 A1 | 11/2010 | Chian et al. | |
| 2010/0291286 A1 | 11/2010 | O'Neill et al. | |
| 2011/0064784 A1 | 3/2011 | Mullens et al. | |
| 2011/0153028 A1 | 6/2011 | Albertorio | |

OTHER PUBLICATIONS

Galante, J. et al. "Sintered Fiber Metal Composites as a Basis for Attachment of Implants to Bone." Journal of Bone and Joint Surgery Am 53 (1971):101-114 (15 pages).

Bobyn, J.D., Pilliar, R.M., Cameron, H.U., and Weatherly, G.C. "The Optimum Pore Size for Fixation of Porous-Surfaced Metal Implants by the Ingrowth of Bone." Clinical Orthopedics and Related Research. 150 (1980): 263-270 (8 pages).

Bobyn, J.D., Stackpool, G.J., Hacking, S.A., Tanzer, M., and Krygier, J.J. "Characteristics of Bone Ingrowth and Interface Mechanics of a New Porous Tantalum Biomaterial." The Journal of Bone & Joint Surgery (Br) vol. 81-B (1999): 907-914 (8 pages).

Hulbert, S.F., Young, F.A., Mathews, R.S., Klawitter, J.J., Talbert, C.D., Stelling, F.H. "Potential of Ceramic Materials as Permanently (56) References Cited

OTHER PUBLICATIONS

Implantable Skeletal Prostheses." Journal of Biomedical Materials Research. 4 (1970): 433-456 (24 pages).
Levine, B. "A New Era in Porous Metals: Applications in Orthopaedics." Advanced Engineering Materials. 10 (2008): 788-792 (5 pages).
"Biofoam Technical Monograph", Cancellous Titanium Matrix, Fixation with Bite, Wright Medical, 2009.
Notification of Transmittal of the International Search Report and the Written Opinion of the International Searching Authority, or the Declaration dated Aug. 6, 2014 for International Application No. PCT/US2014/027796 (14 pages).
Notification of Transmittal of the International Search Report and the Written Opinion of the International Searching Authority, or the Declaration dated Jul. 24, 2014 for International Application No. PCT/US2014/024424 (17 pages).
Extended European Search Report dated Oct. 20, 2016 for European Patent Application No. EP 14 76 9573 (8 pages).
International Preliminary Report on Patentability and the Written Opinion dated Sep. 15, 2015 for International Application No. PCT/US2014/024424 (11 pages).

\* cited by examiner

METHOD OF MANUFACTURING A TUBULAR MEDICAL IMPLANT

CROSS REFERENCE TO RELATED APPLICATIONS

This is a division of U.S. patent application Ser. No. 14/204,056 entitled "A METHOD OF MANUFACTURING A TUBULAR MEDICAL IMPLANT", filed Mar. 11, 2014, which is incorporated herein by reference. U.S. patent application Ser. No. 14/204,056 is a non-provisional application based upon U.S. provisional patent application Ser. No. 61/788,738 entitled "POROUS TUBES", filed Mar. 15, 2013, which is incorporated herein by reference.

BACKGROUND OF THE INVENTION

1. Field of the Invention

The present invention relates to a method of manufacturing medical implants, and, more particularly, to a method of manufacturing tubular medical implants.

2. Description of the Related Art

Medical implants are manufactured incorporating various techniques to produce different shapes using biologically compatible materials. One medical implant shape that is commonly used is that of a tubular structure. Tubular medical implants have a wide range of medically useful applications in orthopaedics, cardiology and other areas. One useful feature incorporated into tubular medical implants is a pore pattern on the surface and throughout the implant. By incorporating porosity into the tubular implant, the implant can be given useful properties such as controlled therapeutic release and/or an interface for cell or tissue growth.

As cell growth mechanics and pharmacokinetics have become better understood, the pore structure of medical implants have become increasingly complex and structured. Such designs requirements of increased complexity have not been met by current production methods, especially in tubular implants that have a relatively high thickness and/or highly variable pore pattern throughout the implant. Of particular difficulty is varying the implant's pore pattern throughout the thickness of the tubular implant.

One known method of producing tubular medical implants with varied porous structures is to take a base tube, such as a stent, and stretch an elastic, porous graft material over the stent. When the graft material is properly positioned over the tube, the stretching force is removed which allows the graft material to return to a less stretched state and form a snug fit on the stent. The graft material can then be sewn on to the graft to create a finished stent graft. A problem with this method is that it limits the materials that can be incorporated into the medical implant, is labor intensive and has the risk of permanently changing the pore sizes on the graft material during stretching.

What is needed in the art is a method that can manufacture tubular medical implants that have complex porous structures from a large variety of materials.

SUMMARY OF THE INVENTION

The present invention provides a method of creating a tubular medical implant by sliding at least a part of a first porous tube within a second porous tube to create overlapped areas between the first and second porous tubes and then bonding the overlapped areas together.

The invention in one form is directed to a method of manufacturing a tubular medical implant including the step of forming a hollow first tube with a first diameter and a first plurality of pores thereon. A hollow second tube is formed with a second unstretched diameter and a second plurality of pores formed thereon. The second unstretched diameter is greater than the first diameter. At least a portion of the first tube is slid within the second tube to create overlapped areas between the first tube and the second tube, which are bonded together.

The invention in another form is directed to a tubular medical implant that includes a first hollow tube, a second hollow tube, and a bonding interface. The first hollow tube includes a first surface with a first plurality of pores formed thereon and the first hollow tube defines a first diameter. The second hollow tube surrounds the first hollow tube and includes a second surface having a second plurality of pores formed thereon. The second hollow tube defines a second unstretched diameter that is greater than the first diameter of the first hollow tube. A bonding interface is formed between the first hollow tube and second hollow tube to hold the hollow tubes together.

An advantage of the present invention is that it provides a method to produce tubular medical devices that have complex porous patterns.

Another advantage is that the method of the present invention allows for precise control of the pore size and distribution in the implant.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
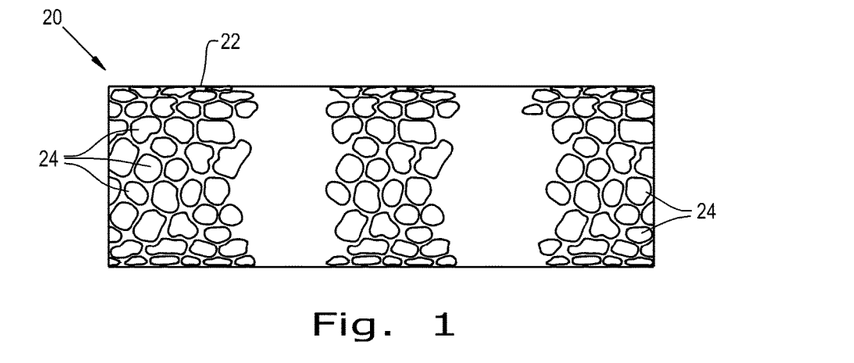
FIG. 1 is a perspective view of a porous tube of the present invention.

Referring now to the drawings, and more particularly to FIG. 1, there is shown a hollow tube 20 which generally includes a tube wall 22 and pores 24 formed in the tube wall 22. As can be seen, the hollow tube 20 has many pores 24 formed through its tube wall 22, but the number of pores 24 can be varied depending on the tube's 20 intended application. The tube wall 22 has a thickness that can be the same throughout the tube 20 or varied. The tube wall 22 can have any thickness suitable for use at a desired implantation site, including a range from about 0.0001" to greater than 0.04". The tube 20 can be made from any suitable biocompatible material, e.g., titanium, titanium alloys, tantalum, tantalum alloys, cobalt chrome alloys, stainless steel, polyaryletherketone polymers (PAEK), polyetheretherketone (PEEK), polyetherketone (PEK), polyetherketoneketone (PEKK), Ultrapek, polyethylene, polyurethane, alumina and zirconia. Once the tube 20 is formed, the pores 24 can be created in the tube wall 22. The pores 24 can be created by a variety of processes, e.g., chemical etching, photochemical etching, laser cutting, electron-beam machining, conventional machining, stamping, extrusion, rolling and knurling.

Figure 2:
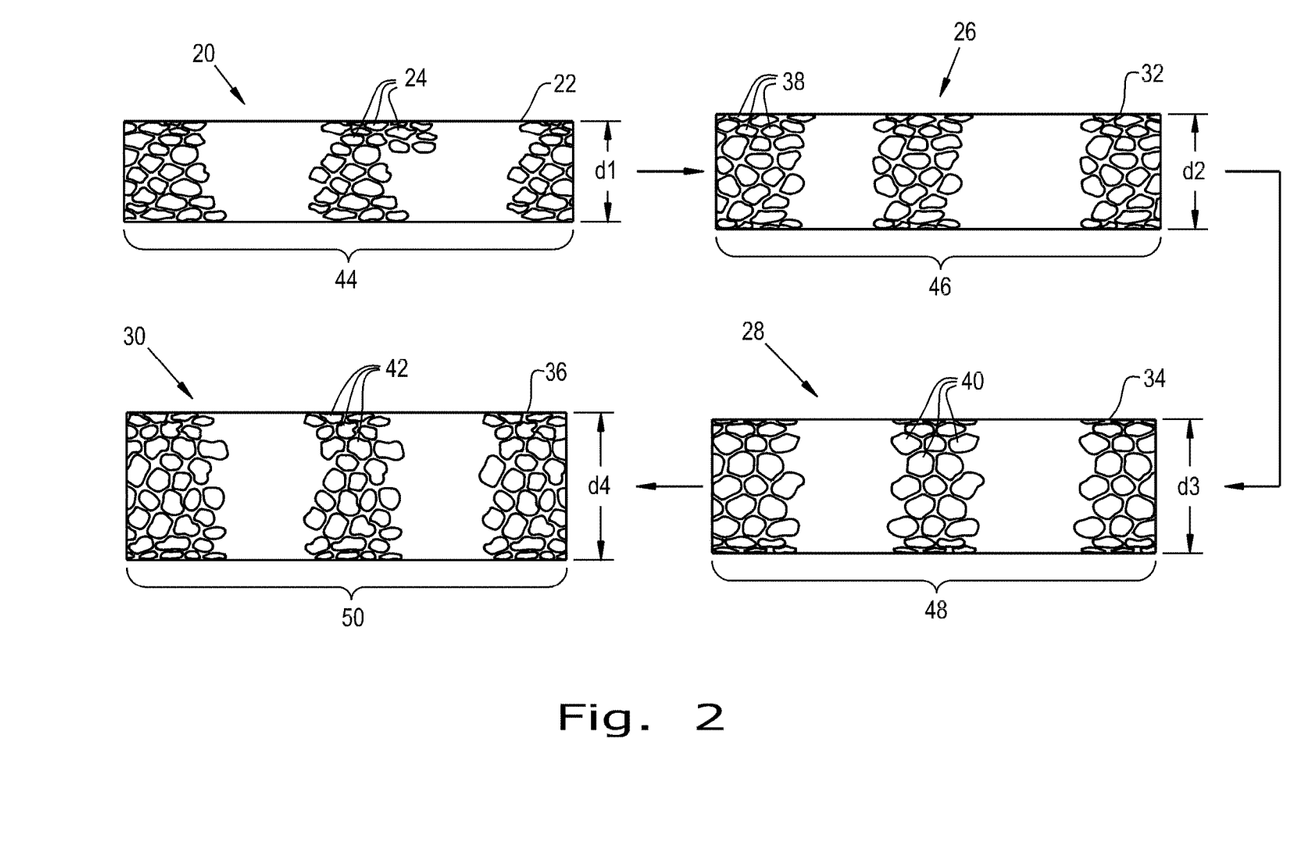
FIG. 2 is a perspective step-by-step view of a method of producing a tubular medical implant according to the present invention.

Referring now to FIG. 2, multiple tubes 20, 26, 28, 30 are shown. Each tube 20, 26, 28, 30 has a respective unstretched diameter d1, d2, d3, d4 and a tube wall 22, 32, 34, 36 with pores 24, 38, 40, 42 forming pore patterns 44, 46, 48, 50. The tubes' diameters d1, d2, d3, and d4 vary, with d1<d2<d3<d4. Preferably d1 is not substantially less (>5%) than d2, d2 is not substantially less than d3, and d3 is not substantially less than d4. Each tube wall 22, 32, 34, 36 has a respective thickness that may or may not be equal to the thickness of the other tube walls. Each tube 20, 26, 28, 30 can be made from the same material or different materials, depending on the implant's intended application.

Figure 3:
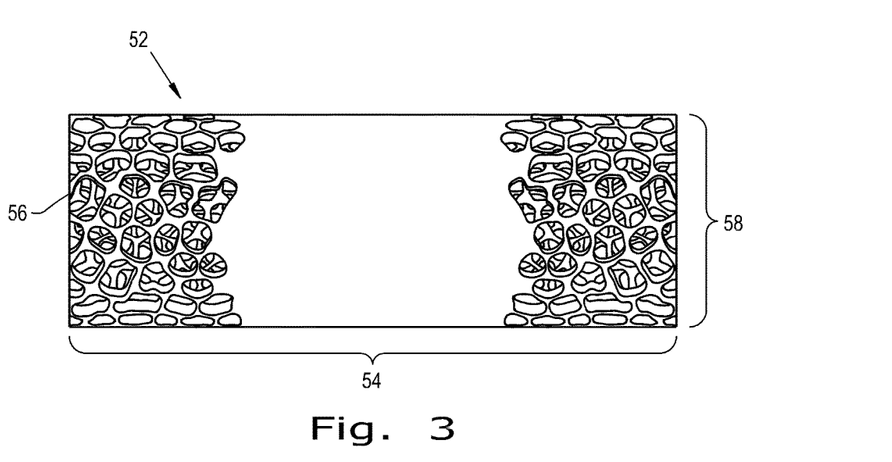
FIG. 3 is a perspective view of the tubular medical implant produced by the method shown in FIG. 2.

To produce a finished porous tubular implant 52 (shown in FIG. 3), the tubes 20, 26, 28 with smaller diameters d1, d2, d3 are placed into the tubes 26, 28, 30 with larger diameters d2, d3, d4 sequentially, and bonded together. For example, tube 20 would first be placed within tube 26 to produce a tube (not shown) that has a tube wall thickness substantially equivalent to the thicknesses of tubes 20 and 26 added together. The produced tube also has a 3-dimensional pore architecture that is a combination of pore patterns 44 and 46. Once tube 20 is placed within tube 26, overlapped areas 54 (shown in FIG. 3) of the tubes 20, 26 are created that can be bonded together to hold tubes 20 and 26 together, if desired, before the intermediate tube is placed within tube 28. Preferably, the diameters d1 and d2 of the tubes 20 and 26 will be relatively similar to each other to allow for a bond interface 56 (shown in FIG. 3) with a negligible thickness or effect on an implant pore pattern 58 of the finished porous tubular implant 52. Once tube 20 is within tube 26, either bonded or not, the tubes 20, 26 are then placed within tube 28, and optionally bonded to tube 28 at overlapped areas. Once tubes 20 and 26 are within tube 28, and optionally bonded, the tubes 20, 26 and 28 are placed within tube 30 and bonded at overlapped areas to form finished tubular implant 52. While finished tubular implant 52 is shown as having the tubes 20, 26, 28 and 30 completely overlapping, it could be desirable to create a tubular implant that has only a partial overlap between some or all of the various component tubes. As previously mentioned, a bond interface 56 is formed between tubes that are bonded together. The bond interface 56 can be formed by the material of tube walls pressing together or be a separable bonding component, such as an adhesive. The method used to bond tubes together can vary based on the tube material(s), but can include, e.g., diffusion bonding, sintering, laser welding, heat staking, thermal processing, ultrasonic welding, mechanical welding and adhesive bonding.

Figure 4:
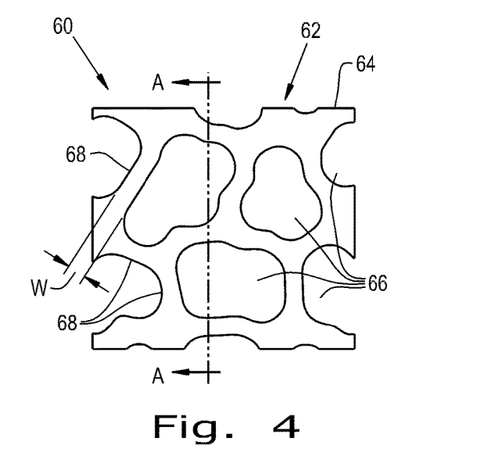
FIG. 4 is a close-up perspective view of a porous tube of the present invention.
Figure 5:
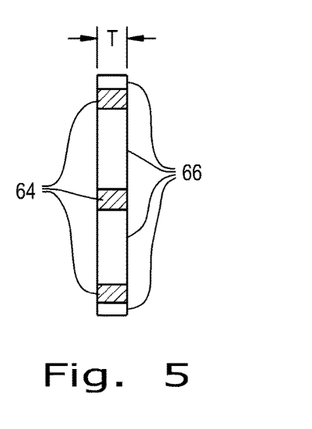
FIG. 5 is a sectional side view of the porous tube shown in FIG. 4 along line A-A.

FIGS. 4 and 5 show one embodiment of a section of a tube 60 according to the present invention. FIG. 4 shows a porous microstructure 62 of the section of a porous thin-walled tube 60 of wall thickness T. For ease of explanation, tube wall 64 is displayed as flat rather than curved. All pores 66 in this tube wall 64 are through-holes. Struts 68 (which can be referred to as scaffold struts) are defined as the bars of material between the pores 66. Strut width W is defined as the smallest dimension of an individual strut 68 on the tube 60 surface. FIG. 5 shows a sectional view of the porous tube 60 in FIG. 4 along line A-A.

Figure 6:
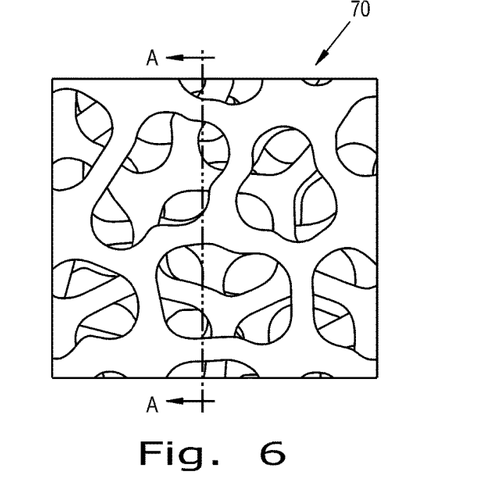
FIG. 6 is a close-up perspective view of another tubular medical implant produced according to the present invention.
Figure 7:
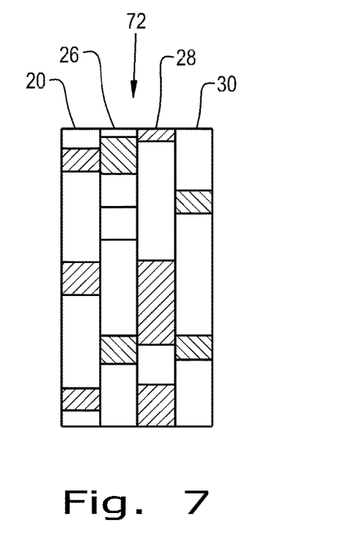
FIG. 7 is a sectional side view of the tubular medical implant shown in FIG. 6 along line A-A.

FIG. 6 shows a section of a resulting porous microstructure 70 of porous tubular implant 52 and FIG. 7 shows a section taken along line A-A in FIG. 6. FIG. 7 thus shows one tube wall 72 including four thin-walled tubes 20, 26, 28, 30. The other side of the tube 72 across the diameter of the tube 72 is not shown in FIGS. 6 and 7; in other words, the longitudinal axis of the thin-walled tube can be, for example, to the right of the sectional view in FIG. 7, and the longitudinal axis of the assembled tube 72 can be, for example, to the right of the sectional view in FIG. 7.

Figure 8:
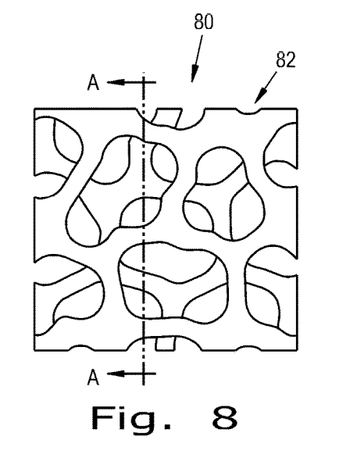
FIG. 8 is a close-up perspective view of another porous tube of the present invention.
Figure 9:
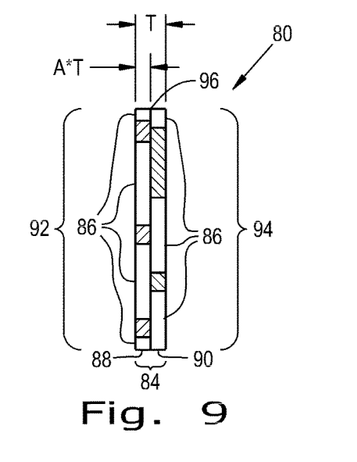
FIG. 9 is a sectional side view of the porous tube shown in FIG. 8 along line A-A.

FIGS. 8 and 9 shows another embodiment of a tube 80 according to the present invention. FIG. 8 shows a porous microstructure 82. FIG. 9 shows a portion of a porous thin-walled tube 80 of wall thickness T. For ease of explanation, the tube wall 84 is displayed as flat rather than curved. Pores 86 are then created in the tube 80 from both sides 88, 90 of an individual thin-walled tube 80. Different patterns are used to create the pores 86 on each side 88, 90 of the tube 80. A first pore pattern 92 from the outside of the tube 80 transitions to a second pore pattern 94 from the inside of the tube 80 at some location 96 within the tube wall 84. This location 96 is defined as A*T, where coefficient A is some fraction of the wall thickness. Coefficient A can range from just greater than 0 to just less than 1. Typically, coefficient A will most likely be on the order of 0.35-0.65.

Figure 10:
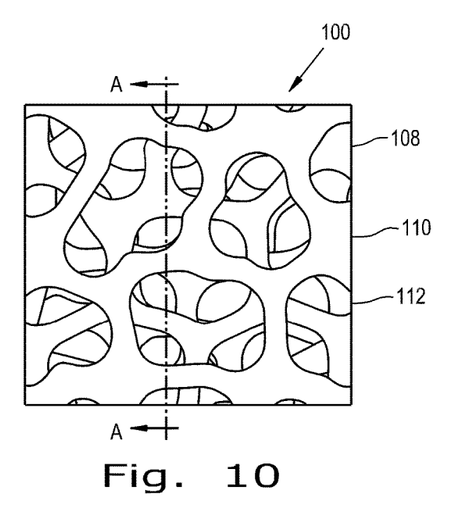
FIG. 10 is a close-up perspective view of yet another tubular medical implant produced according to the present invention.

To generate a three-dimensional porous tube 100 as shown in FIG. 10, individual thin-walled tubes such as in FIG. 8 are bonded together. In this embodiment of the invention, pore patterns 101, 102, 104, 106 are formed on adjacent sides of adjacent tubes 108, 110, 112 (see FIG. 11). For the three thin-walled tubes 108, 110, 112 bonded together, shown in FIG. 11, tube 108 has pore pattern 101 on a first side 114, and pore pattern 102 on a second side 116. Tube 110 has pore pattern 102 on a first side 118 and pore pattern 104 on a second side 120. Tube 112 has pore pattern 104 on a first side 122 pore pattern 106 on a second side 124.

Figure 11:
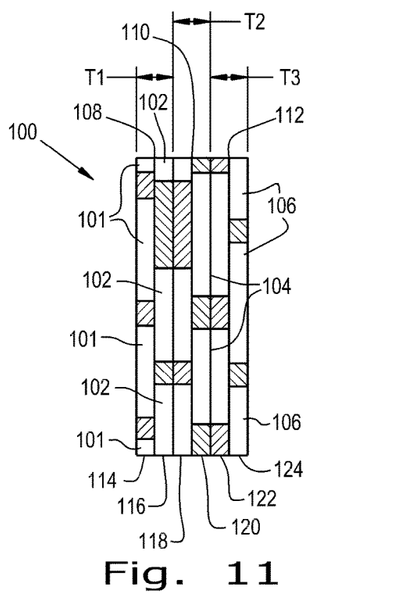
FIG. 11 is a sectional side view of the tubular medical implant shown in FIG. 10 along line A-A.

Thus, adjacent thin-walled tubes 108, 110, 112 mate up against identical pore geometries. While the pore patterns 101, 102, 104, 106 of the thin-walled tubes 108, 110, 112 are shown in FIG. 11 as being aligned to identical pore patterns on adjacent thin-walled tubes 108, 110, 112, the present invention also contemplates mating a tube to another tube with an identical pore pattern on a first side of the tube and a different tube with a non-identical pore pattern on a second side of the tube. The pore patterns 101, 102, 104, 106 can all overlap to create an implant pore (unnumbered) that extends completely through the formed tube wall of porous tube 100.

Figure 12:
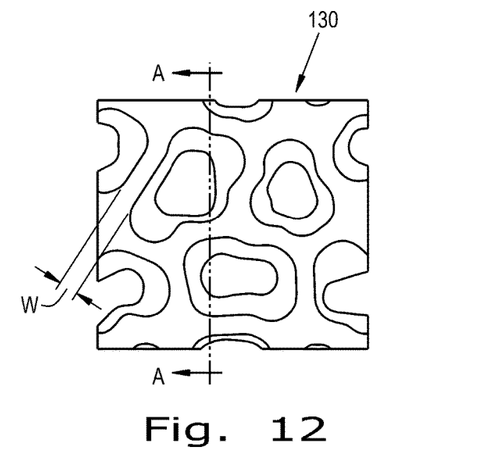
FIG. 12 is a close-up perspective view of yet another porous tube of the present invention.
Figure 13:
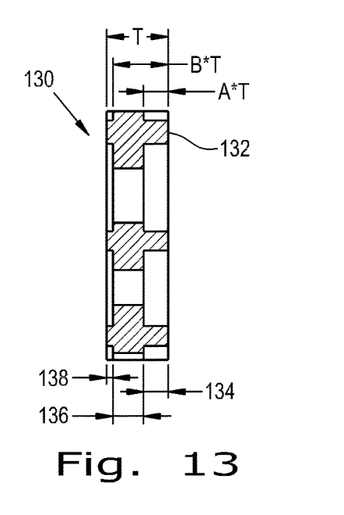
FIG. 13 is a sectional side view of the porous tube shown in FIG. 12 along line A-A.

FIGS. 12 and 13 show another embodiment of a tube 130 according to the present invention. Within a given thin-walled tube 130 of wall thickness T, as can be seen in FIG. 13, the geometry adjacent to a surface 132 can be denoted as a first pore pattern 134. At a thickness of A*T, where coefficient A is some fraction of the tube wall thickness T, first pore pattern 134 transitions to a second geometry (pore pattern) 136. Likewise, at a thickness of B*T, where coefficient B is some fraction of the tube wall thickness T, second pore pattern 136 transitions to a third geometry (pore pattern) 138. The values of coefficients A and B are such that 0<A<B<1. The third pore pattern 138 can be different from or identical to the first pore pattern 134.

Figure 14:
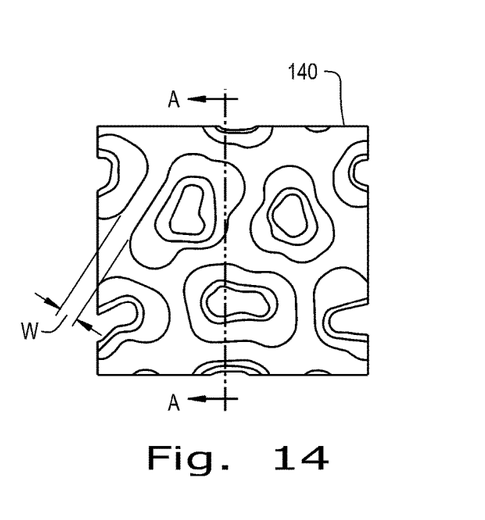
FIG. 14 is a close-up perspective view of yet another porous tube of the present invention.
Figure 15:
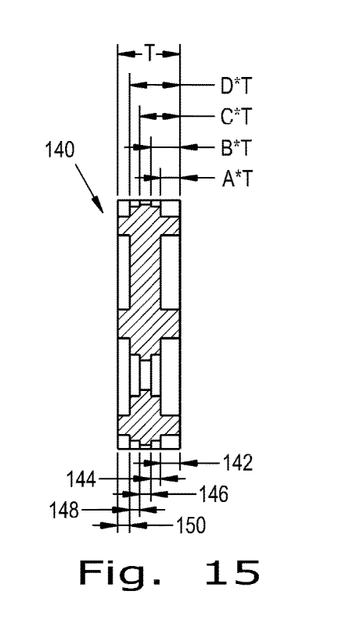
FIG. 15 is a sectional side view of the porous tube shown in FIG. 14.

The method of the present invention contemplates any number of different geometries being included in a tube wall. FIGS. 14 and 15 show a tube wall 140 with five different geometries 142, 144, 146, 148, 150 through a wall thickness T. Geometries 142, 144, 146 and 148 can have respective fraction coefficients A, B, C, D of thickness T that represent the fractional thickness of the corresponding geometry, which can be defined by 0<A<B<C<D<1. Thus, the thickness of geometry 142 is A*T, the thickness of geometry 144 is B*T, the thickness of geometry 146 is C*T, and the thickness of geometry 148 is D*T.

As described throughout, the number of tubes that can be bonded together according to the present invention to form a porous tubular implant can be varied from a small number (2) of tubes to a large number (>10) of tubes.

The present invention in one form provides a bone or tissue scaffold including a plurality of layers bonded to one another, each layer having a different pore pattern formed on each side of the layer, adjacent sides of adjacent layers having substantially identical pore patterns which thus align with one another over the course of at least two (for example, two, three, or more) adjacent layers, each layer being formed as a tube, each tube being concentric relative to the other tubes.

Clinically acceptable bone ingrowth or on-growth surfaces such as BioSync™ marketed by Sites Medical, beads, plasma spray, or other similar bone or tissue ingrowth or on-growth surfaces can be used.

The manufacturing method described herein may be used for other purposes as well. One alternative use of this method includes creating a structure that has a layer(s)/tube(s) that is not porous all the way through, or that when aligned (for example, a respective layer) with an adjacent layer a barrier is created to prevent bone or other material, such as a lower melting temperature material, from passing through. In this way, to one side of the barrier, tissue ingrowth can occur; to the other side of the barrier, the lower melting temperature material (which can form a structure beyond the pores) can be retained in the pores.

Another alternative use of this method includes creating a structure including a layer(s)/tube(s) in the "middle" which has recesses and/or porous sections and including outer layer(s)/tube(s) which are generally solid. The purposes of this include the following: (a) to create a material or product that is lighter by removing material from the wall thickness while leaving the outer or working surfaces unaffected; (b) to create a material or product that has more flexibility and strength in a lighter weight configuration than otherwise possible because of the other size constraints; (c) to provide a method to create regions inside of a product for storage of different materials for a variety of purposes, both medically and non-medically related. While this method is described in the general application of a tube, this feature can be applied to flat, curved, or other similar geometries.

Figure 16:
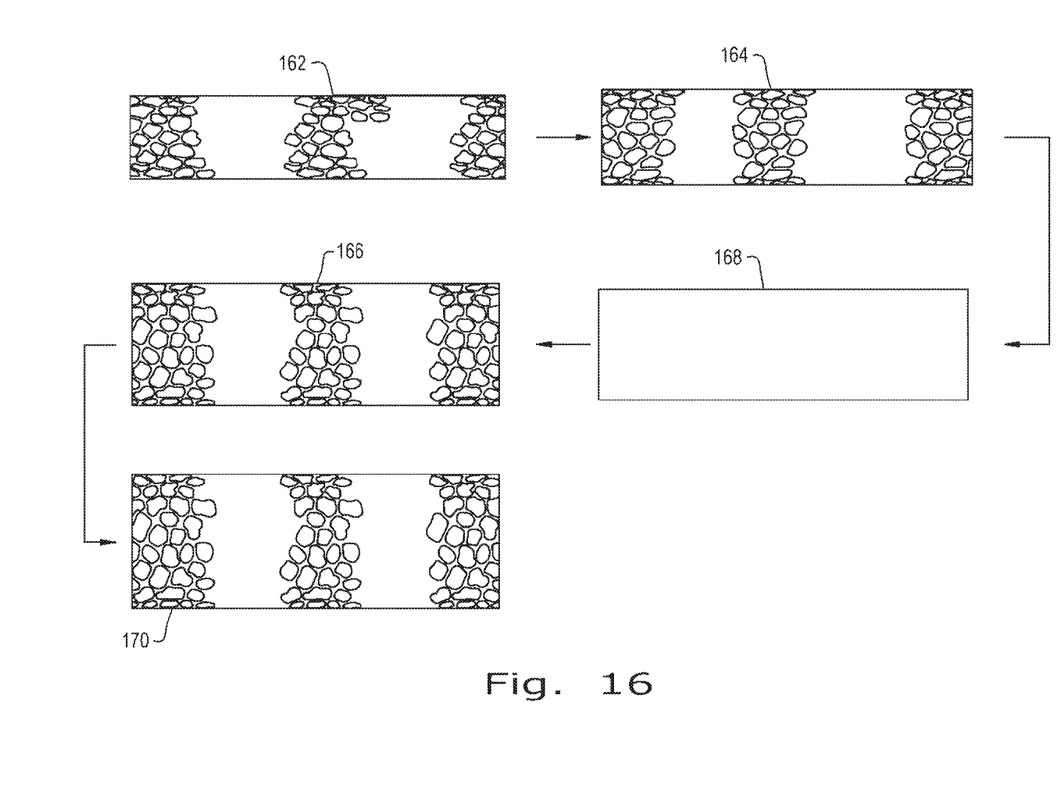
FIG. 16 a perspective step-by-step view of a method of producing another tubular medical implant according to the present invention.
Figure 17:
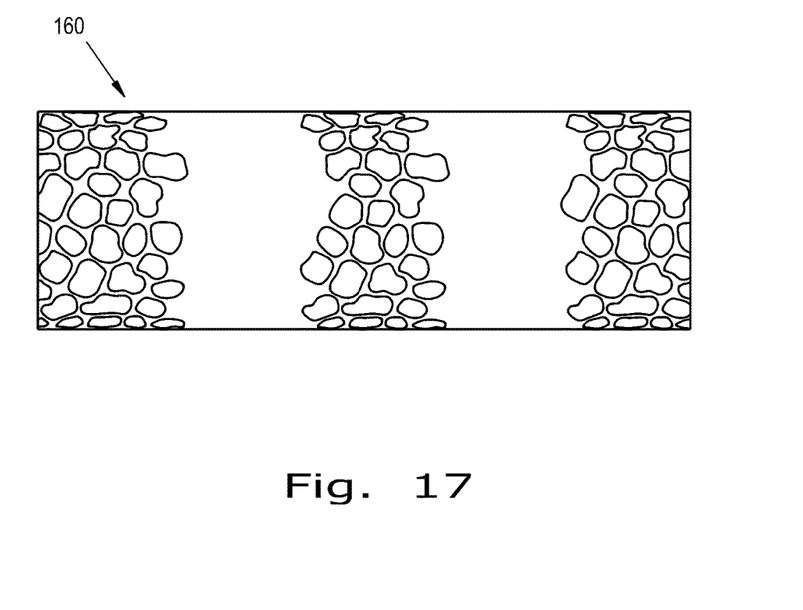
FIG. 17 is a perspective view of the tubular medical implant produced by the method shown in FIG. 16.

FIGS. 16 and 17 illustrate a tubular medical implant 160 incorporating porous tubes 162, 164, 166 and a non-porous rod 168, which may be hollow. Porous tube 162 is placed within porous tube 164, and optionally bonded together, before being placed within non-porous rod 168. Non-porous rod 168 can act as a barrier to prevent ingrowth of tissues into porous tubes 162 and 164, but can also act as a support rod when placed within porous tube 166 if other tubes, such as tube 170, are being press fitted to porous tube 166. In such a case, non-porous rod 168 can provide strength to resist collapse of porous tube 166 when a pressing pressure and a pressing temperature are applied to the porous tube 166 to press fit tube 170 on to porous tube 166. Non-porous rod 168 could also be a solid rod acting as a core for porous tubes 166, 170 stacked on top.

Further, in another embodiment of the present invention, the scaffold of the present invention can be attached (for example, by way of diffusion bonding) to a substrate (such as an implant). The substrate can be an implant and can be made of a variety of materials, including, but not limited to, titanium and/or CoCr.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tubular medical implant, comprising:
a first hollow tube including a first tube wall with a first plurality of pores formed thereon, said first hollow tube defining a first diameter;
a second hollow tube surrounding and press fit to said first hollow tube to form an overlapped area and including a second tube wall with a second plurality of pores formed thereon, said second hollow tube defining a second unstretched diameter that is greater than said first diameter, at least one of said first plurality of pores and at least one of said second plurality of pores overlapping within said overlapped area to form an implant pore extending completely through said first tube wall and said second tube wall;
a non-porous rod supporting an interior of said first hollow tube, wherein said non-porous rod is hollow; and
a third hollow tube placed within said non-porous rod and including a third tube wall with a third plurality of pores formed thereon.

2. The tubular medical implant of claim 1, wherein said first plurality of pores forms an inner pore pattern and said second plurality of pores forms an outer pore pattern.

3. The tubular medical implant of claim 2, wherein said inner pore pattern and said outer pore pattern together form a plurality of implant pores forming a tubular implant pore pattern.

4. The tubular medical implant of claim 1, wherein said at least one of said first plurality of pores and said at least one of said second plurality of pores partially overlap.

5. The tubular medical implant of claim 1, wherein said press fit of said second hollow tube to said first hollow tube does not deform said first plurality of pores and said second plurality of pores.

6. The tubular medical implant of claim 1, wherein said first hollow tube is composed of at least one of a polymer, a metal, and a ceramic and said second hollow tube is composed of at least one of a polymer, a metal, and a ceramic.

7. The tubular medical implant of claim 1, wherein said first hollow tube defines a first tube thickness and said second hollow tube defines a second tube thickness which is equal to said first tube thickness.

8. A tubular medical implant comprising:
a first hollow tube including a first tube wall with a first plurality of pores formed thereon, said first hollow tube defining a first diameter;
a second hollow tube surrounding and press fit to said first hollow tube to form an overlapped area and including a second tube wall with a second plurality of pores formed thereon, said second hollow tube defining a second unstretched diameter that is greater than said first diameter, at least one of said first plurality of pores and at least one of said second plurality of pores overlapping within said overlapped area to form an implant pore extending completely through said first tube wall and said second tube wall; and
a third hollow tube at least partially surrounding said second hollow tube and including a third tube wall with a third plurality of pores formed thereon.

9. The tubular medical implant of claim 8, wherein said third hollow tube is press fit to said second hollow tube.

10. The tubular medical implant of claim 8, wherein at least one of said third plurality of pores overlaps with said implant pore.

* * * * *

UNITED STATES PATENT AND TRADEMARK OFFICE
CERTIFICATE OF CORRECTION

PATENT NO. : 10,449,065 B2  
APPLICATION NO. : 15/620226  
DATED : October 22, 2019  
INVENTOR(S) : Troy D. Knapp et al.

It is certified that error appears in the above-identified patent and that said Letters Patent is hereby corrected as shown below:

On the Title Page

Page 2 - Item (56) References Cited - U.S. PATENT DOCUMENTS:  
At 6,306,424 B1, please delete "Vyakamam et al.", and substitute therefor --Vyakarnam et al.--;  
At 6,333,029 B1, please delete "Vyakamam et al.", and substitute therefor --Vyakarnam et al.--;  
At 6,365,149 B2, please delete "Vyakamam et al.", and substitute therefor --Vyakarnam et al.--;  
At 6,534,084 B1, please delete "Vyakamam et al.", and substitute therefor --Vyakarnam et al.--;  
At 6,712,850 B2, please delete "Vyakamam et al.", and substitute therefor --Vyakarnam et al.--.

Signed and Sealed this  
Twenty-second Day of December, 2020

Andrei Iancu  
*Director of the United States Patent and Trademark Office*